(12) United States Patent  (10) Patent No.: US 8,383,549 B2
Parrish et al.  (45) Date of Patent: Feb. 26, 2013

(54) METHODS OF INCREASING CROP YIELD AND CONTROLLING THE GROWTH OF WEEDS USING A POLYMER COMPOSITE FILM

(75) Inventors: Mark Parrish, Raleigh, NC (US); Ralf Dujardin, Duesseldorf (DE)

(73) Assignees: Bayer Cropscience LP, Research Triangle Park, NC (US); Bayer Innovation GmbH, Duesseldorf (DE)

( * ) Notice: Subject to any disclaimer, the term of this patent is extended or adjusted under 35 U.S.C. 154(b) by 106 days.

(21) Appl. No.: 12/909,065

(22) Filed: Oct. 21, 2010

(65) Prior Publication Data

US 2011/0152100 A1 Jun. 23, 2011

Related U.S. Application Data

(63) Continuation-in-part of application No. 12/176,070, filed on Jul. 18, 2008, which is a continuation-in-part of application No. 12/175,276, filed on Jul. 17, 2008.

(60) Provisional application No. 60/951,016, filed on Jul. 20, 2007, provisional application No. 60/956,755, filed on Aug. 20, 2007.

(51) Int. Cl.
*A01N 43/54* (2006.01)
*A01N 47/36* (2006.01)

(52) U.S. Cl. ........... 504/136; 47/8; 47/26; 47/901; 424/405; 424/409; 424/411; 504/215; 504/216; 523/132

(58) Field of Classification Search .............. None
See application file for complete search history.

(56) References Cited

U.S. PATENT DOCUMENTS

| | | | |
|---|---|---|---|
| 849,685 | A | 4/1907 | Johnson |
| 3,159,601 | A | 12/1964 | Ashby |
| 3,159,602 | A | 12/1964 | Hamilton et al. |
| 3,220,972 | A | 11/1965 | Lamoreaux |
| 3,284,406 | A | 11/1966 | Nelson |
| 3,377,432 | A | 4/1968 | Abbott et al. |
| 3,419,593 | A | 12/1968 | Willing |
| 3,436,366 | A | 4/1969 | Modic |
| 3,697,473 | A | 10/1972 | Polmanteer et al. |
| 3,715,334 | A | 2/1973 | Karstedt |
| 3,814,730 | A | 6/1974 | Karstedt |

(Continued)

FOREIGN PATENT DOCUMENTS

| | | |
|---|---|---|
| DE | 28 19 515 A1 | 12/1978 |
| DE | 195 00 402 A1 | 11/1996 |

(Continued)

OTHER PUBLICATIONS

International Search Report for PCT/EP08/05545, dated Feb. 12, 2008.

(Continued)

*Primary Examiner* — Neil Levy
(74) *Attorney, Agent, or Firm* — Baker Donelson Bearman, Caldwell & Berkowitz, PC

(57) ABSTRACT

Methods of protecting a crop from weed infestation, controlling weed growth, reducing fumigant dosage in crop protection, and reducing the growth of weeds by applying a polymer composite material with or without a biocide to soil, a crop, a vegetable, a weed, or combinations thereof are provided. In an aspect, the disclosure provides for a polymer composite material including a base polymer coated with:
(1) a first barrier layer;
(2) a second layer with our without a biocide; and
(3) a third protective layer.

14 Claims, 3 Drawing Sheets

U.S. PATENT DOCUMENTS

| | | | |
|---|---|---|---|
| 4,199,548 A | 4/1980 | Kaiho et al. | |
| 4,340,709 A | 7/1982 | Jeram et al. | |
| 4,538,531 A | 9/1985 | Wong | |
| 4,819,374 A | 4/1989 | Gemgnani | |
| 4,942,068 A | 7/1990 | Schweicher et al. | |
| 5,705,092 A | 1/1998 | Wellinghoff et al. | |
| 5,866,269 A * | 2/1999 | Dalebroux et al. | 428/537.5 |
| 5,906,865 A | 5/1999 | Ellermeier et al. | |
| 6,046,243 A | 4/2000 | Wellinghoff et al. | |
| 6,296,865 B1 | 10/2001 | Dujardin et al. | |
| 6,737,491 B2 | 5/2004 | Soerens et al. | |
| 6,808,801 B2 | 10/2004 | George et al. | |
| 6,849,685 B2 | 2/2005 | Soerens et al. | |
| 6,887,961 B2 | 5/2005 | Soerens et al. | |
| 6,964,803 B2 | 11/2005 | Krautkramer et al. | |
| 7,115,321 B2 | 10/2006 | Soerens et al. | |
| 7,205,259 B2 | 4/2007 | Soerens | |
| 2005/0227026 A1 | 10/2005 | Finestone | |
| 2007/0203191 A1 | 8/2007 | Loso et al. | |
| 2007/0299264 A1 | 12/2007 | Huang et al. | |
| 2010/0240705 A1 | 9/2010 | Jeschke et al. | |

FOREIGN PATENT DOCUMENTS

| | | | |
|---|---|---|---|
| DE | 696 29 891 T2 | | 7/2004 |
| EP | 0 057 459 | | 8/1982 |
| EP | 0 188 978 | | 7/1986 |
| EP | 0 190 530 | | 8/1986 |
| EP | 0 214 507 A2 | | 3/1987 |
| EP | 0 249 694 A2 | | 12/1987 |
| EP | 0 275 015 A2 | | 7/1988 |
| EP | 0 539 588 A1 | | 5/1993 |
| EP | 0 938 935 A2 | | 9/1999 |
| EP | 1 023 949 A1 | | 1/2000 |
| FR | 1528464 | | 7/1968 |
| FR | 2372874 | | 6/1978 |
| FR | 2668106 | | 4/1992 |
| GB | 1378663 | * | 9/1972 |
| GB | 2383304 | | 6/2003 |
| GB | 2397805 | | 8/2004 |
| JP | 63-175072 A | | 7/1988 |
| WO | 97/28634 A1 | | 8/1997 |
| WO | 97/29634 A1 | | 8/1997 |
| WO | 99/32286 A1 | | 7/1999 |
| WO | 99/47595 A1 | | 9/1999 |
| WO | 03/088747 A1 | | 10/2003 |
| WO | 2007/095229 A2 | | 8/2007 |
| WO | 2007/115643 A1 | | 10/2007 |
| WO | 2007/115644 A1 | | 10/2007 |
| WO | 2007/115646 A1 | | 10/2007 |
| WO | 2007/149134 A1 | | 12/2007 |

OTHER PUBLICATIONS

"Directive 98/8EC of the European Parliament and of the Council of Feb. 16, 1998 concerning the Placing of Biocidal Products on the Market," Official Journal of the European Communitites, Apr. 24, 1998, pp. 1-63.

* cited by examiner

METHODS OF INCREASING CROP YIELD AND CONTROLLING THE GROWTH OF WEEDS USING A POLYMER COMPOSITE FILM

CROSS REFERENCE TO RELATED APPLICATIONS

This application is a Continuation-in-Part of U.S. patent application Ser. No. 12/176,070, filed on Jul. 18, 2008, which claims priority to U.S. application Ser. No. 60/951,016 filed on Jul. 20, 2007, and U.S. patent application Ser. No. 12/175,276, filed Jul. 17, 2008, which claims priority to U.S. Provisional Appl. No. 60/956,755, filed Aug. 20, 2007, and U.S. Provisional Appl. No. 60/951,016, filed Jul. 20, 2007, the content of each of these applications is herein incorporated by reference in their entireties.

BACKGROUND

1. Field of the Invention

In an aspect, the present invention relates to polymer composite materials with biocide functionality, methods for producing such polymer composite materials and their use, in particular, for agriculture.

2. Description of Related Art

A wide variety of polymer materials like biodegradable mulch films for reducing weed growth or special biodegradable horticulture pots are known which are used in the field of agriculture. An emphasis in the equipment of these polymer materials lies in the task either to stabilize the material against environmental and chemical influences or to improve the biodegradability of the material. Examples for agricultural films stabilized against pesticides with an additive can be found in Japanese application JP 631 75 072. In the European patent application EP 0214507 there are UV stabilizers described which are used in films for outdoor agriculture.

An example of a material capable of thermal diffusion of an active ingredient is described in DE 28 19 515 A1. A multi-layered composite material comprises a layer which is able to increase the temperature within the material by exothermic chemical reaction so that a functional material can be set free. However, the disclosed inorganic chemical substances which are needed for the exothermic reaction are harmful to the environment as well as unsuitable for the production, harvest or transport of food and medical articles.

Another polymer material incorporating biocide inorganic substances is known from DE 696 29 891 T2. There, chlorine dioxide is provided as biocide inorganic substance to act as a disinfectant in films for food packaging. However, the handling and controlling of the right amount of disinfectant over a given time period is difficult complex and costly. According to the disclosed material it involves different layers which must include a hydrophobic layer comprising an acid freeing substance and a neighbouring hydrophilic layer comprising chlorinate ions.

Another approach to functionalize agricultural or horticultural polymers lies in the incorporation of inorganic substances like copper, copper salts and finely pulverized silver acting as disinfectants. However, the release of the active substance is incontrollable and often involves the degradation or dissolving of the polymer.

All yet known polymer materials in agriculture or horticulture share the problem that the lifespan of the functionalized material is short. Moreover, the function often only lies in the protection of the polymer itself. However, a function for the agricultural goods like that of a biocide is not given in a convenient way because of the limitation to only inorganic substances, again involving degradable or soluble polymers to set free the inorganic substance. Like that, a lifespan required for a growing season of 12 months or in case of reuse of several years and/or over several planting and harvesting seasons of the functionalized polymer material is impossible. The mechanical properties decrease over time with increasing biodegradation causing a molecular weight reduction of the polymer. Molecular weight reduction reducing desired polymer performance like strength necessary for mitigation of weather fluctuations by agricultural films or protecting the roots of seedlings by nursery pots and trays, for example.

SUMMARY

Therefore, it is the object of the present invention to provide a polymer composite material, preferably for the use in agriculture and horticulture, which can have a variety of biocide functionalities and which has a long lifespan.

It is another object of the present invention to provide a method for the production of such a polymer composite material.

In an aspect, this object is solved by a polymer composite material with biocide functionality, preferably for the use in agriculture, comprising at least one base polymer compound and, at least one biocide active ingredient, wherein the biocide active ingredient is an organic biocide that can be emitted from the polymer composite material by diffusion and/or osmosis. In another aspect, the disclosure provides for a polymer composite material without a biocide.

DETAILED DESCRIPTION

Figure 1:
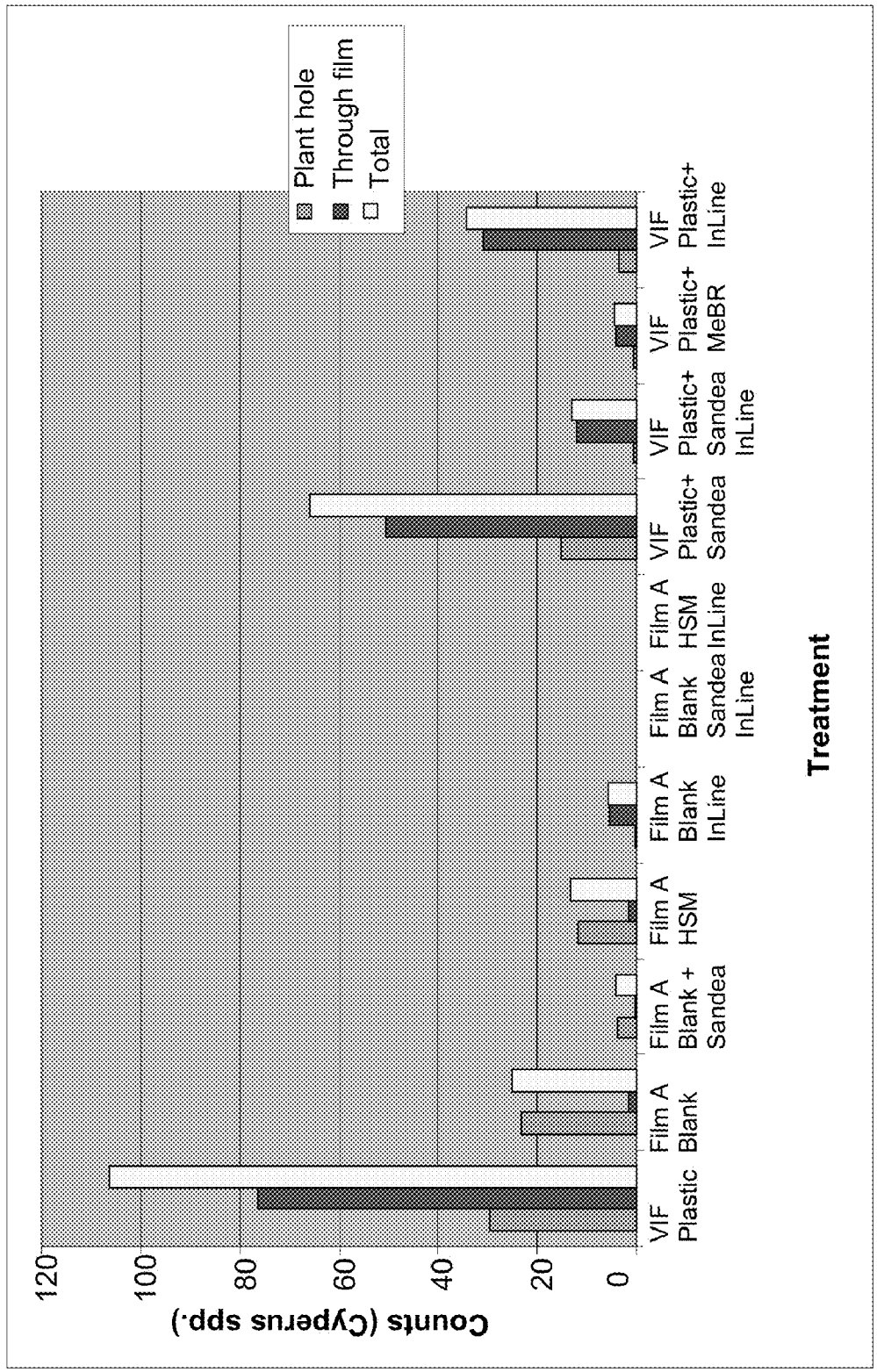
FIG. 1 provides an analysis of weed control of a polymer composite material according to the disclosure with or without incorporation of herbicide verses conventional plastic mulch or VIF.

Under the term base polymer compound all polymer compounds are understood which show a sufficient UV and weather stability to withstand constant outdoor exposure at least for 12 months and do not react with the organic biocide active ingredient and whose properties are not changed by the organic biocide. As the flexibility of polymer material is dependent upon the material thickness, flexible films as well as inflexible molded articles are understood under the term base polymer material.

Under the term biocide active ingredient there are all chemical substances understood which are capable of killing different forms of living organisms and/or viruses used in fields such as medicine, agriculture, and forestry.

In a preferred embodiment of the present invention the biocide active ingredient or a combination of biocide active ingredients is incorporated in the polymer composite material in form of a molecular dispersion. Like that, an even and defined distribution in the composite material is achieved.

In another preferred embodiment of the present invention the biocide active ingredient is incorporated into a coating layer.

By that means the emission of the biocide active ingredient by diffusion and/or osmosis can be facilitated and/or timed.

Coating materials are preferably applied in a thin film (thickness of the dry coating layer preferably below 0.5 mm) to the base polymer compounds. In order to achieve the desired characteristics from the thin film, the coating material formulation and the coating layer structure can be tailored in relation to the desired part characteristics, e.g. flexible films or rigid molded parts to facilitate and/or time the emission of the biocide active ingredient. Coating materials can be formulated from a wide variety of chemicals and materials or a combination of different chemicals and applied as single layer or stacked multilayer. Coating materials of the present invention are preferably formulated from four components: binders, additives, biocide active ingredients and the carrier fluid.

Binders primarily function as an adhesive to the base polymer. Binders are polymer adhesive systems with varying molecular weights. The molecules in the binder can be crosslinked during the curing stage to improve strength and create the polymer composite material.

In the preferred embodiment of the present invention the coating material can be based on water soluble polymer adhesive systems comprising binders which are cross-linkable and which are after cross-linking water insoluble but water-swellable and capable of gel-forming by water absorbing. The term "cross-linkable" according to the present invention indicates that the binders can foam a network structure preferably initiated by heat, pressure, radiation and/or chemicals (hereinafter also referred to as hardener). The term "gel-forming" according to the present invention refers to a colloid structure comprising at least 50%, at least 75% and typically at least 95% wt liquid, which is immobilized by surface tension between it and a macromolecular network of fibres built from a small amount of binders. In a preferred embodiment the liquid of the gel is water and the gel is a hydrogel in which water is the dispersion medium.

The binders are preferably selected from the group comprising gelatin; alginates; cellulose based polymers such as methyl cellulose, hydroxymethyl cellulose, carboxymethylcellulose, cellulose acetate phthalate, and the like; starch based polymers such as carboxymethyl starch; natural gums, such as gum arabic, locust bean gum, carrageenan gum and xanthan gum; pectins; polymers formed from acid-group containing monomers, such as poly(acrylates) (including poly(acrylic acid), poly(methacrylic acid), and the like), poly(ethers), poly(acrylamides), poly(vinyl alcohol), maleic anhydride copolymers, poly(vinyl sulfonates), hydrolyzed acrylonitrile grafted starch, acrylic acid grafted starch, poly(N-vinyl pyrrolidone), poly(-hydroxyethylacrylate), poly(2-hydroxyethyl-methacrylate), poly(sodium acrylate-co-acrylic acid), poly(vinylsulfonic acid), poly(ethyleneoxide), block co-polymers of ethylene oxide with polyamides, polyesters, and polyurethanes, and salt forms mixtures and copolymers of the above.

Particularly preferred binders comprise water soluble (but after crosslinking insoluble) chemical and/or physical cross-linkable adhesive polymers such as polyvinyl alcohol, polyvinyl methyl ether; polyvinyl pyrrolidone; polyethylene oxide; cellulose derivatives such as dextrans and starches; polyacrylates such as polyacrylacid, polyacrylamides, methyl cellulose, carboxy methyl cellulose, starch-based polymers, gelatin, casein, xanthan hydroxyl-ethyl-cellulose hydroxylpropyl cellulose and/or dispersions from block co-polymers of ethylene oxide with polyurethane.

Illustrative examples of particularly useful gel-forming, water absorbing cross-linkable coating binders that are capable, under the most favorable conditions, of absorbing at least about 5, more preferably at least 10, even more preferably at least 15 and most preferably at least 25 times its weight in an aqueous solution containing 0.9 weight percent sodium chloride are preferably selected from the group comprising superabsorbers such as poly(acrylates) including poly(acrylic acid), poly(methacrylic acid), and the like), maleic anhydride copolymers, poly(vinyl sulfonates), poly(sodium acrylate-co-acrylic acid), poly(vinylsulfonic acid), (as for example described in U.S. Pat. No. 6,737,491, U.S. Pat. No. 6,849,685, U.S. Pat. No. 6,887,961, U.S. Pat. No. 7,115,321, U.S. Pat. No. 6,964,803, U.S. Pat. No. 6,808,801, U.S. Pat. No. 7,205,259, each of these references are hereby incorporated by reference in their entirety), gelatin and/or dispersions from block co-polymers of ethylene oxide with polyurethane.

A particularly useful coating material according to the present invention comprises the combination of at least two water absorbent cross-linkable polymer binders, wherein one water absorbent cross-linkable polymer binder is gelatin. In a particularly preferred embodiment coating layers comprise the combination of a gelatin binder and a superabsorber binder such as a poly(acrylates) binder.

Gelatin has been shown to be surprisingly beneficial as it supports the attachment of the water absorbent cross-linkable polymers to the base polymer without substantially interfering with the properties of the water absorbent cross-linkable polymers.

Any gelatin such as photographic gelatin, feed gelatin, edible gelatin, industrial gelatin, protein gelatin can be used for such a preferred coating layer. By adding as an additive a hardener, the gelatin is cross-linked due to a reaction of free amino-, imino- and hydroxyl groups.

Additives are defined as insoluble pigments or low molecular weight chemicals in coating formulations that allow coatings to perform specific functions but do not contribute to the biocide function. Additives include but are not limited to pigments. Pigments are typically the colorant portion of a coating material, but can also perform corrosion protection or stability in ultraviolet (UV) light. Additives also include but are not limited to non-pigments. Non-pigment additives include stabilizers to block attacks of ultraviolet light or heat, hardener to speed up the cross-linking reaction, co-solvents to increase viscosity, or plasticizers to improve uniform coating.

In a further preferred embodiment of the invention, a hardener, preferably formaldehyde is used as an additive to crosslink the coating layer material and to improve the attachment of the layer material to the base polymer.

A particularly useful composite material relates to a base polymer wherein the coating materials comprise a combination of water absorbent cross-linkable polymers, preferably superabsorbers, more preferably polyacrylates, gelatin and a hardener, preferably formaldehyde.

The carrier fluid is typically a liquid such as an organic solvent or water. The carrier fluid allows the coating materials to flow and be applied by methods such as spraying, dipping, cascade and/or curtain casting. This component may be in the coating formulation before application, but evaporates afterwards to allow the solid materials to immobilize and form the coating layer. The resulting polymer composite material can optionally be dried.

The carrier fluid might therefore be completely absent, partially present or present in the final, ready-to-use polymer composite material. In a preferred embodiment the carrier fluid is absent or only partially present in the final, ready-to-use polymer composite material. However, the skilled person in the art acknowledges that water or another liquid will be absorbed by the polymer composite material during use and will play an important role for the functionality of the polymer composite material.

In a further preferred embodiment of the invention the organic solvent is, ethanol, aceton, 1,4-dioxane, tetrahydrofuran, dichlormethane, acetonitrile, dimethylformamide, dimethylsulfoxide, acetic acid, n-butanol, isopropanol, n-propanol, methanol, formic acid, other solvents known to the skilled person in the art and/or aqueous solutions thereof.

In an aspect, coating materials of the present invention comprise at least one biocide active ingredient (hereinafter also referred to as a biocide).

Coating formulations vary widely, with different types and amounts of binders, additives, carrier fluids and biocide active ingredients. The differences in coating formulations provide film characteristics specifically set for the part and its end-use. Often, one type of coating material cannot be formulated to provide all of the desired properties. Several layers of different coating materials may be applied to a base polymer to form the coating film.

The polymer composite material according to another preferred embodiment of the present invention can be a multi-layered coating structure and the biocide active ingredient is incorporated into repeating or one coating layers.

By the incorporation of the biocide active ingredient into repeating coating layers a control of diffusion and/or osmosis rates is even better achievable. Apart from that, different biocide active ingredients can be incorporated in different layers. The present invention, however, also relates to an embodiment wherein a mixture of at least two biocide active ingredients are incorporated into one coating layer. Depending on the plant growth and the possible seasonally changing requirements in terms of pests, fungi, and the like, a tailored approach to biocide treatment can be provided.

In a preferred embodiment of the invention, the at least one biocide active ingredient can be incorporated into the same coating layer as the binders. In an embodiment, the layer with the at least one biocide comprises gelatin.

The organic biocide is preferably selected from the group consisting of pesticides, herbicides, insecticides, algicides, fungicides, moluscicides, miticides, and rodenticides. Moreover, the organic biocide can even more preferably be selected from the group consisting of germicides, antibiotics, antibacterials, antivirals, antifungals, antiseptics, antiprotozoals, and antiparasites.

In another preferred embodiment of the invention the organic biocide is selected from the group of antiseptics and/or disinfectants for medical use and food.

As the regulations for chemical substances being considered safe for the use in the agricultural, food and medical field are constantly changing, such organic biocide active ingredients are most preferred for the present invention which comply with the actual official regulations for chemical substances and especially for antiseptics and disinfectants in those fields. Especially those substances which are listed in the European the Biocidal Products Directive (98/8/EC) by the European Commission are preferably used as biocide active ingredients according to the present invention.

In another preferred embodiment of the present invention the organic biocide is selected from the group comprising of acetamides and anilides herbicides, thiocarbamate herbicides, chlorphenoxy herbicides, dipyridyl herbicides, dinitrocresolic herbicides, cyclohexyloxim herbicides, phosphonate herbicides, traizolon herbicides, urea herbicide derivatives and/or mixtures thereof.

Particular herbicides according to the present invention are selected from the group comprising acetochlor, acibenzolar, acibenzolar-s-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammoniumsulfamat, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chlorid, chlomitrofen, chlorophthalim, chlorthaldimethyl, chlorotoluron, chlorsulfuron, cinidon, cinidon-ethyl, cinmethylin, cinosulfuron, clethodim, clodinafop clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-p, diclofop, diclofop-methyl, diclofop-p-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-p, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, eptc, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chlor-4-fluor-5-[4-(3fluorpropyl)-4,5-dihydro-5-oxo-1H-tetrazol-1-yl-]-phenyl]-ethansulfonamid, fenoprop, fenoxaprop, fenoxaprop-p, fenoxaprop-ethyl, fenoxaprop-p-ethyl, fentrazamide, fenuron, flamprop, flamprop-m-isopropyl, flamprop-m-methyl, flazasulfuron, florasulam, fluazifop, fluazifop-p, fluazifop-butyl, fluazifop-p-butyl, fluazolate, flucarbazone, flucarbazone-sodium, flucetosulfuron, fluchloralin, flufenacet (thiafluamide), flufenpyr, flufenpyr-ethyl, flumetralin, flumetsulaam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellinic acid, glufosinate, 1-glufosinate, 1-glufosinate-ammonium, glufosinate-ammonium, glyphosate, glyphosate-isopropylammonium, H-9201, halosafen, halosulfuron, halosulfuron-methyl, haloxyfop, haloxyfop-p, haloxyfop-ethoxyethyl, haloxyfop-p-ethoxyethyl, haloxyfop-methyl, haloxyfop-p- methyl, hexazinone, hnpc-9908, HOK-201, HW-02, imazamethabenz, imazamethabenz-methyl, imazamox, imazapic, imazapyr, imazaquin, imazethapyr, imazosulfuron, inabenfide, indanofan, indolacetic acid (IAA), 4-indol-3-yl-butanoic acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleinic acid hydrazid, MCPA, MCPB, MCPB-methyl, -ethyl and -sodium, mecoprop, mecoprop-sodium, mecoprop-butotyl, mecoprop-p-butotyl, mecoprop-p-dimethylammonium, mecoprop-p-2-ethylhexyl, mecoprop-p-kalium, mefenacet, mefluidide, mepiquat-chlorid, mesosulfuron, mesosulfuron-methyl, mesotrione, methabenzthiazuron, metam, metamifop, metamitron, metazachlor, methazole, methoxyphenone, methyldymron, 1-methylcyclopropen, methylisothiocyanat, metobenzuron, metobenzuron, metobromuron, metolachlor, s-metolachlor, metosulam, metoxuron, metribuzin, metsulfuron, metsulfuron-methyl, molinate, monalide, monocarbamide, monocarbamide-dihydrogensulfat, monolinuron, monosulfuron, monuron, MT 128, MT-5950, i.e. N-[3-chlor-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (mixture of isomers), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichlorid, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-p, quizalofop-p-ethyl, quizalofop-p-tefuryl, rimsulfuron, secbumeton, sethoxydim, siduron, simazine, simetryn, SN-106279, sulcotrione, sulfallate (cdec), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, th-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichlor acetic acid (tca), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-p, vernolate, ZJ-0166, ZJ-0270, ZJ-0543, ZJ-0862, as well as the following compounds

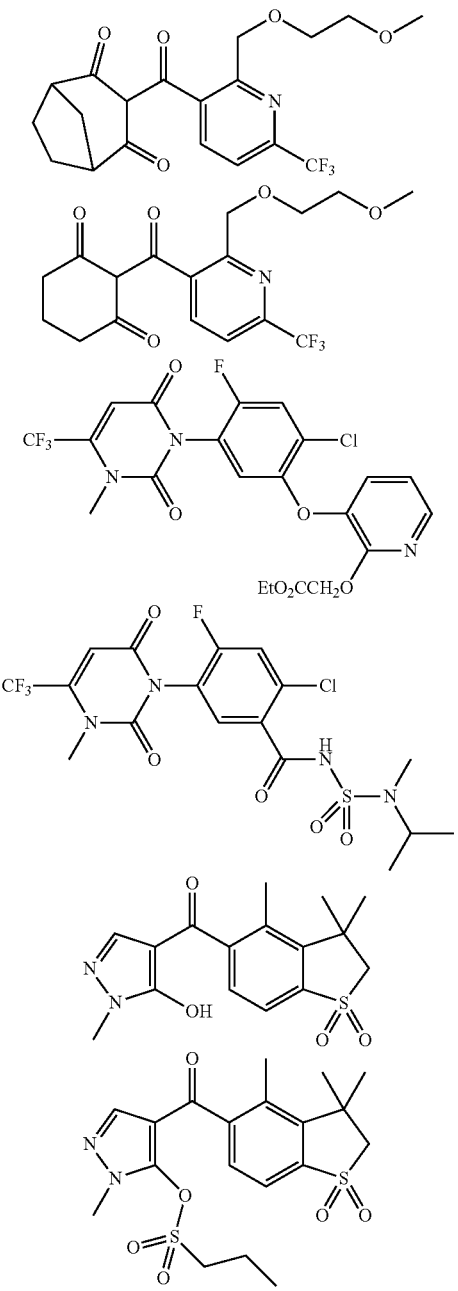

In another preferred embodiment of the present invention the organic biocide is selected from the group comprising antibiotics insecticides cyclodien insecticides, insect growth regulators, carbamate insecticides, nicotenoide insecticides, pyrethroid herbicides, oxadiazine insecticides, organophosphorus insecticides and/or mixtures thereof.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus*; Hymenopterons, such as *Sirex juvencus, Urocerus gigas, Urocerus gigas taignus, Urocerus augur;* Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*; Bristletails, such as *Lepisma saccharina*.

Particular insecticides according to the present invention are selected from the group comprising acetylcholinesterase (ACNE) inhibitors such as for example carbamates, e.g. alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, and xylylcarb; or organophosphates, e.g. acephate, azamethiphos, azinphos(-methyl, -ethyl), bromophos-ethyl, bromfenvinfos(-methyl), butathiofos, cadusafos, carbophenothion, chlorethoxyfos, chlorfenvinphos, chlormephos, chlorpyrifos(-methyl/-ethyl), coumaphos, cyanofenphos, cyanophos, chlorfenvinphos, demeton-5-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl, O-salicylate, isoxathion, malathion, mecarbam, methacrifos, methamidophos, methidathion, mevinphos, monocrotophos, naled, omethoate, oxydemeton-methyl, parathion(-methyl/-ethyl), phenthoate, phorate, phosalone, phosmet, phosphamidon, phosphocarb, phoxim, pirimiphos(-methyl/ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, and imicyafos. GABA-gated chloride channel antagonists such as for example organochlorines, e.g. camphechlor, chlordane, endosulfan, gamma-HCH, HCH, heptachlor, lindane, and methoxychlor; or fiproles (phenylpyrazoles), e.g. acetoprole, ethiprole, fipronil, pyrafluprole, pyriprole, and vaniliprole. Sodium channel modulators/voltage-dependent sodium channel blockers, such as for example pyrethroids, e.g. acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrin (pyrethrum), eflusilanat; DDT; or methoxychlor. Nicotinergic acetylcholine receptor agonists/antagonists such as for example chloronicotinyls, e.g. acetamiprid, clothianidin, dinotefuran, imidacloprid, imidaclothiz, nitenpyram, nithiazine, thiacloprid, thiamethoxam, AKD-1022, nicotine, bensultap, cartap, thiosultap-sodium, and thiocylam. Allosteric acetylcholine receptor modulators (agonists) such as for example spinosyns, e.g. spinosad and spinetoram. Chloride channel activators, such as for example mectins/macrolides, e.g. abamectin, emamectin, emamectin benzoate, ivermectin, lepimectin, and milbemectin; or juvenile hormone analogues, e.g. hydroprene, kinoprene, methoprene, epofenonane, triprene, fenoxycarb, pyriproxifen, and diofenolan.

Active ingredients with unknown or non-specific mechanisms of action such as for example gassing agents, e.g. methyl bromide, chloropicrin and sulfuryl fluoride; selective antifeedants, e.g. cryolite, pymetrozine, pyrifluquinazon and flonicamid; or mite growth inhibitors, e.g. clofentezine, hexythiazox, etoxazole. Oxidative phosphorylation inhibitors, ATP disruptors such as for example diafenthiuron; organotin compounds, e.g. azocyclotin, cyhexatin and fenbutatin oxide; or propargite, tetradifon. Oxidative phoshorylation decouplers acting by interrupting the H proton gradient such as for example chlorfenapyr, binapacryl, dinobuton, dinocap and DNOC. Microbial disruptors of the insect gut membrane such as for example *Bacillus thuringiensis* strains. Chitin biosynthesis inhibitors such as for example benzoylureas, e.g. bistrifluoron, chlorfluazuron, diflubenzuron, fluazuron, flucycloxuron, flufenoxuron, hexaflumuron, lufenuron, novaluron, noviflumuron, penfluoron, teflubenzuron or trifluvmuron. Buprofezin. Moulting disruptors such as for example cyromazine. Ecdysone agonists/disruptors such as for example diacylhydrazines, e.g. chromafenozide, halofenozide, methoxyfenozide, tebufenozide, and JS-118; or azadirachtin. Octopaminergic agonists such as for example amitraz. Site III electron transport inhibitors/site II electron transport inhibitors such as for example hydramethylnon; acequinocyl; fluacrypyrim; or cyflumetofen and cyenopyrafen. Electron transport inhibitors such as for example Site I electron transport inhibitors, from the group of the METI acaricides, e.g. fenazaquin, fenpyroximate, pyrimidifen, pyridaben, tebufenpyrad, tolfenpyrad, and rotenone; or voltage-dependent sodium channel blockers, e.g. indoxacarb and metaflumizone. Fatty acid biosynthesis inhibitors such as for example tetronic acid derivatives, e.g. spirodiclofen and spiromesifen; or tetramic acid derivatives, e.g. spirotetramat. Neuronal inhibitors with unknown mechanism of action, e.g. bifenazate. Ryanodine receptor effectors such as for example diamides, e.g. flubendiamide, (R),(S)-3-chloro-N1-{2-methyl-4-[1,2,2,2-tetrafluoro-1-(trifluoromethyl)e-thyl]phenyl}-N2-(1-methyl-2-methylsulphonylethyl)phthalamide, chlorantraniliprole (Rynaxypyr), or Cyazypyr. Further active ingredients with unknown mechanism of action such as for example amidoflumet, benclothiaz, benzoximate, bromopropylate, buprofezin, chinomethionat, chlordimeform, chlorobenzilate, clothiazoben, cycloprene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene or verbutine; or one of the following known active compounds 4-{[(6-brompyrid-3-yl)methyl](2-fluorethy)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethy)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5- fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-λ4-sulfanylidencyanamid (known from WO 2007/149134), [1-(6-chlorpyridin-3-yl)ethyl](methyl)oxido-λ4-sulfanylidencyanamid (known from WO 2007/149134) and its diastereomeres (A) and (B)

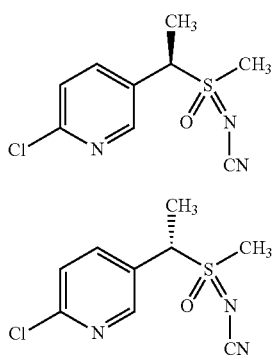

(also known from WO 2007/149134), [(6-trifluormethylpyridin-3-yl)methyl](methyl)oxido-λ4-sulfanyliden-cyanamid (known from WO 2007/095229), or [1-(6-trifluormethylpyridin-3-yl)ethyl](methyl)oxido-λ4-sulfanylidencyanamid (known from WO 2007/149134) and its diastereomeres (C) and (D)

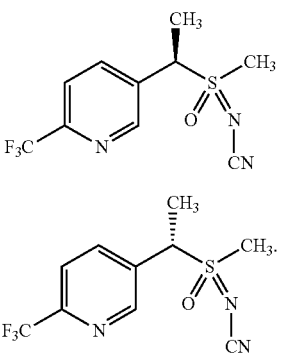

(also known from WO 2007/149134).

In another preferred embodiment of the present invention the organic biocide is selected from the group comprising acetamide and anilide fungicides, aliphatic nitrogen fungicides, aromatic fungicides, thiocarbamate fungicides, oxazol fungicides, organophosphorous fungicides, phatlimid fungicides, strobillurin fungicides, urea derivative fungicides, quaternary ammonium antiseptic compounds, quaternary ammonium related antiseptic compounds like chlorhexidine gluconate, polyhexamethylene biguanide hydrochloride, octenidine dihydrochloride and/or mixtures thereof.

Particular fungicides according to the present invention are selected from the group comprising inhibitors of the nucleic acid synthesis such as for example benalaxyl, benalaxyl-M, bupirimate, clozylacon, dimethirimol, ethirimol, furalaxyl, hymexazol, mefenoxam, metalaxyl, metalaxyl-M, oflurace, oxadixyl and oxolinic acid. Inhibitors of the mitosis and cell division such as for example benomyl, carbendazim, chlorfenazole, diethofencarb, ethaboxam, fuberidazole, profenofos, pencycuron, thiabendazole, thiophanate, thiophanate-methyl and zoxamide. Inhibitors of the respiration such as for example diflumetorim as CI-respiration inhibitor; bixafen, boscalid, carboxin, fenfuram, flutolanil, fluopyram, furametpyr, furmecyclox, mepronil, oxycarboxin, penthiopyrad, thifluzamide as CII-respiration inhibitor; amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor. Compounds capable to act as an uncoupler such as like for example dinocap, fluazinam and meptyldinocap. Inhibitors of the ATP production such as for example fentin acetate, fentin chloride, fentin hydroxide, and silthiofam. Inhibitors of the amino acid and/or protein biosynthesis such as for example andoprim, blasticidin-S, cyprodinil, kasugamycin, kasugamycin hydrochloride hydrate, mepanipyrim and pyrimethanil. Inhibitors of the signal transduction such as for example fenpiclonil, fludioxonil and quinoxyfen. Inhibitors of the lipid and membrane synthesis such as for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin. Inhibitors of the ergosterol biosynthesis such as for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole. Inhibitors of the cell wall synthesis such as for example benthiavalicarb, dimethomorph, flumorph, iprovalicarb, mandipropamid, polyoxins, polyoxorim, validamycin A, and valiphenal. Inhibitors of the melanine biosynthesis such as for example carpropamid, diclocymet, fenoxanil, phthalide, pyroquilon and tricyclazole. Compounds capable to induce a host defense such as like for example acibenzolar-5-methyl probenazole, and tiadinil. Compounds capable to have a multisite action such as like for example Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations including calcium polysulphide, thiram, tolylfluanid, zineb and ziram. Further compounds like for example 3-(difluoromethyl)-1-methyl-N-[(9R)-9-(1-methylethyl)-1,2,3,4-tetrahydro-1,4-methanonaphthalen-5-yl]-1H-pyrazole-4-carboxamide, 3-(difluoromethyl)-1-methyl-N-[(9S)-9-(1-methylethyl)-1,2,3,4-tetrahydro-1,4-methanonaphthalen-5-yl]-1H-pyrazole-4-carboxamide, 3-(difluoromethyl)-N-[4'-(3,3-dimethylbut-1-yn-1-yl)biphenyl-2-yl]-1-meth-yl-1H-pyrazole-4-carboxamide, 2-chloro-N-(4'-prop-1-yn-1-ylbiphenyl-2-yl)pyridine-3-carboxamide, 2-chloro-N-[4'-(3,3-dimethylbut-1-yn-1-yl)biphenyl-2-yl]pyridine-3-carbox-amide, 5-fluoro-1,3-dimethyl-N-(4'-prop-1-yn-1-ylbiphenyl-2-yl)-1H-pyrazol-e-4-carboxamide, N-[4'-(3,3-dimethylbut-1-yn-1-yl)biphenyl-2-yl]-5-fluoro-1,3-dimethyl-1H-pyrazole-4-carboxamide, 3-(difluorom-ethyl)-1-methyl-N-(4'-prop-1-yn-1-ylbiphenyl-2-yl)-1H-pyrazol-e-4-carboxamide, 3-(difluoromethyl)-N-[4'-(3-methoxy-3-methylbut-1-yn-1-yl)biphenyl-2-yl]-1-methyl-1H-pyrazole-4-carboxamide, N-(3-tert-butyl-2-ethenylphenyl)-1-methyl-3-(trifluoromethyl)-1H-pyrazole-4-carboxamide, 1-methyl-N-[9-(1-methylethyl)-1,2,3,4-tetrahydro-1,4-methanonaphthalen-5-yl]-3-(trifluoromethyl)-4,5-dihydro-1H-pyrazole-4-carboxamide, N-(4'-chlorobiphenyl-2-yl)-1-methyl-3-(trifluoromethyl)-4,5-dihydro-1H-py-razole-4-carboxamide, N-[9-(dichlorom-ethylidene)-1,2,3,4-tetrahydro-1,4-methanonaphthalen-5-yl]-3-(difluoromethyl)-1-methyl-1H-pyrazole-4-carboxamide, N-[4'-(3-cyano-3-methylbut-1-yn-1-yl) biphenyl-2-yl]-3-(difluoromethyl)-1-methyl-1H-pyrazole-4-carboxamide, rel-3-(difluoromethyl)-1-methyl-N-[(1R,4S)-4-(1-methylethyl)-1,2,3,4-tetr-ahydro-1,4-methanonaphthalen-5-yl]-1H-pyrazole-4-carboxamide, N-[9-(dibromomethylidene)-1,2,3,4-tetrahydro-1,4-methanonaphthalen-5-yl]-3-(difluoromethyl)-1-methyl-1H-pyrazole-4-carboxamide, rel-3-(difluoromethyl)-1-methyl-N-[(1R,4S)-9-methylidene-1,2,3,4-tetrahyd-ro-1,4-methanonaphthalen-5-yl]-1H-pyrazole-4-carboxamide, rel-3-(difluoromethyl)-1-methyl-N-[(1R,4S)-1,2,3,4-tetrahydro-1,4-methano-naphthalen-5-yl]-1H-pyrazole-4-carboxamide, 3-(difluoromethyl)-N-[9-(difluoromethylidene)-1,2,3,4-tetrahydro-1,4-meth-anonaphthalen-5-yl]-1-methyl-1H-pyrazole-4-carboxamide, N-[2-(1,3-dimethylbutyl)phenyl]-5-fluoro-1,3-dimethyl-1H-pyrazole-4-carbo-xamide, N-{2-[1,1'-bi(cyclopropyl)-2-yl]phenyl}-3-(difluoromethyl)-1-methy-1-1H-pyrazole-4-carboxamide, (2E)-2-(2-{[6-(3-chloro-2-methylphenoxy)-5-fluoropyrimidin-4-yl]oxy}pheny-1)-2-(methoxyimino)-N-methylethanamide, 2-chloro-N-(1,1,3-trimethyl-2,3-dihydro-1H-inden-4-yl)pyridine-3-carboxam-ide, N-(3-ethyl-3,5,5-trimethylcyclohexyl)-3-(formylamino)-2-hydroxybenzam-ide, 5-methoxy-2-methyl-4-(2-{[({(1E)1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl-]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylid-ene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'{2-methyl-5-(trifluoromethyl)-4-[3-(trimethylsilyl)propoxy]phenyl}imidoformamide, N-ethyl-N-methyl-N'-{2-methyl-5-(trifluoromethyl)-4-[3-(trimethylsilyl)pr-opoxy]phenyl}imidoformamide, N'-{5-(difluoromethyl)-2-methyl-4-[3-(trimethylsilyl)propoxy]phenyl}-N-et-hyl-N-methylimidoformamide, O-{1-[(4-methoxyphenoxy)methyl]-2,2-dimethylpropyl}1H-imidazole-1-carboth-ioate, N-[2-(4-{[3-(4-chlorophenyl)prop-2-yn-1-yl]oxy}-3-methoxyphenyl)eth-yl]-N2-(methylsulfonyl)valinamide, 5-chloro-6-(2,4,6-trifluorophenyl)-N-[(1R)-1,2,2-trimethylpropyl][1,2,4]t-riazolo[1,5-a]pyrimidin-7-amine, 5-chloro-N-[(1R)-1,2-dimethylpropyl]-6-(2,4,6-trifluorophenyl)[1,2,4]tria-zolo[1,5-a]pyrimidin-7-amine, 5-chloro-7-(4-methylpiperidin-1-yl)-6-(2,4,6-trifluorophenyl)[1,2,4]triaz-olo[1,5-a]pyrimi-dine, propamocarb-fosetyl, (2E)-2-{2-[({[(1E)-1-(3-{[(E)-1-fluoro-2-phenylethenyl]oxy}phenyl)ethylid-ene]amino}oxy)methyl]phenyl}-2-(methoxyimino)-N-methylethanamide, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-p-yrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-py-razole-4-carboxamide, 3,4,5-trichloro-pyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl-}-3-methoxyacrylate, methyl isothiocyanate, metrafenone, mildiomycin, N-(4-chloro-2-nitrophenyl)N-ethyl-4-methyl-benzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)pheny-1]propanamide, N-[(5-bromo-3-chloropyridin-2-yl)methyl]-2,4-dichloropyridine-3-carboxami-de, N-[1-(5-bromo-3-chloropyridin-2-yl)ethyl]-2,4-dichloropyridine-3-carbo-xamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl-]methyl}-2-phenylacetamide, N-{(E)-[(cyclopropylmethoxy)imino][6-(difluoromethoxy)-2,3-difluorophenyl-]methyl}-2-phenylacetamide, natamycin, nickel dimethyldithiocarbamate, nitrothal-isopropyl, octhilinone, oxamocarb, oxyfenthiin, pentachlorophenol and salts, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazol-e-1-carbothioate, tecloftalam, tecnazene, triazoxide, trichlamide, 5-chloro-N'-phenyl-N'-prop-2-yn-1-ylthiophene-2-sulfonohydrazide and zarilamid, 8-hydroxyquinoline-sulphate, 2,3-dibutyl-6-chloro-thieno[2,3-d]pyrimidin-4(3H)one, chloroneb, prothiocarb, binapacryl, and cyprosulfamide.

Common names are used in accordance with the International Organization for Standardization (ISO) or the chemical names, if appropriate together with a customary code number of the compounds and always comprise all applicable forms such as acids, salts, ester, or modifications such as isomers, like stereoisomers and optical isomers.

The biocide active ingredients of the present invention may further possess asymmetric carbons, and thus encompass optical isomers. Additionally, the biocide active ingredients which may be used according to the invention can be present in different polymorphic forms or as a mixture of different polymorphic forms. Both the pure polymorphs and the polymorph mixtures are suitable according to the invention.

The biocide active ingredient which is suitable according to the invention may be formulated and/or applied with one or more additional biocide active ingredient, compound or synergist. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish. Additional compounds include, without limitation, other pesticides, plant growth regulators, fertilizers, soil conditioners, or other agricultural chemicals. Synergists are compounds which increase the action of the biocide active ingredient, without it being necessary for the synergistic agent added to be active itself.

Some of the biocide active ingredients which are suitable according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas.

Some of the biocide active ingredients which are suitable according to the invention also have a strong insecticidal action against insects which destroy industrial materials. Industrial materials in the present connection are to be understood as meaning non-living materials, such as, preferably, plastics, adhesives, sizes, papers and cardboards, leather, wood and processed wood products and coating compositions.

In another preferred embodiment the composite material of the present invention comprises at least one biocide active ingredient that is efficient against insecticidal action of insects which destroy the base polymer.

The biocide active ingredients which are suitable according to the invention can likewise be employed for protecting composite materials which come into contact with seawater or brackish water, such as hulls, screens, nets, buildings, moorings and signaling systems, against fouling.

Furthermore, some of the biocide active ingredients which are suitable according to the invention, alone or in combinations with other active compounds, may be employed as antifouling agents.

Most preferably, the biocide active ingredient of the present invention is a non-liquid non-oil substance at room temperature with low volatility whereby the substance can be solid or can be formulated as a substance in solid form. The choice of such substances improves the release controllability and the storage stability of the polymer composite material. Especially, essential oils as biocide active ingredients should be avoided because of the difficulty to provide a stable dispersion in the polymer base compound or coating layer without exudation of the biocide. Furthermore, the mechanical stability of the polymer composite material could be deterred in the production process due to bubble wrap and the like if liquids or substances with high volatility would be incorporated.

The base polymer compound according to the present invention can be selected from the group consisting of polyethylene terephthalate, polyvinyl chloride, polyolefins such as polyethylene (such as for example LDPE, HDPE) and polypropylene, polystyrene, polyester, polyether, polyacrylate, polycarbonate, polyamide and polyurethane which can optionally comprise commonly used pigments, UV stabilizers, UV absorbers, IR absorber and light diffuser. These materials show the required resistance to outdoor exposure and can be used in form of flexible films as wells as molded inflexible articles like trays and pots.

According to another preferred embodiment of the invention the coating layer has a water uptake of at least 100% per given coating layer area. Like that, it is possible to provide the mobility required for an effective emission of the organic biocide to the target pest or weed by diffusion and/or osmosis.

Preferably, the coating layer is based on a super-absorbent polymer coating material.

Like that, the water uptake and the timing of water loss during outdoor exposure can be tailored.

In a further preferred embodiment of the invention, the base polymer is Corona treated to enhance the attachment of the coating layer(s) to the base polymer.

Additive(s), binder(s) and the at least one biocide can be incorporated in any coating layer of the base polymer. A particularly preferred embodiment of the present invention is a Corona treated base polymer comprising at least one coating layer with a binder, preferably superabsorbers and at least one coating layer with at least one biocide active ingredient. In a preferred embodiment, the base polymer further comprises at least one coating layer with an additive, preferably a hardener (for closing-off). In another preferred embodiment at least one of these coating layers further comprises gelatin. In a more preferred embodiment of the invention all three layers further comprise gelatin.

Preferably the thickness of the whole coating layer with binder(s), preferably superabsorbers and preferably also with gelatin is between 1-100 µm, preferably 5-40 µm, and particularly preferred 10-30 µm. The whole coating layer can be produced by coating several layers of binder(s), preferably superabsorbers and preferably also gelatin for example with cascade or curtain casting. The thickness of the whole coating layer with at least one biocide active ingredient and preferably also gelatin is 0.5-5 µm, preferably 1-4 µm, and particularly preferred 2-3 µm. The whole coating layer with biocide(s) and preferably also with gelatin can be produced by coating several layers of the same or different biocide(s) and preferably with gelatin for example with cascade or curtain casting. The thickness of the whole coating layer with the additive, preferably the hardener is 0.2-5 µm, preferably 0.5-4 µm, even more preferably 2-3 µm. The whole coating layer with the additive, preferably hardener and preferably also with gelatin can be produced by coating several layers of the hardener and preferably with gelatin for example with cascade or curtain casting.

The base polymer has a thickness of 10 to 250 µm, preferably 10 to 150 µm, and more preferably of 20 to 120 µm, and even more preferably 20-50 µm.

In another preferred embodiment of the invention, the base polymer is preferably on both sides Corona treated and has on both sides at least two layers comprising at least one coating layer with binder(s), preferably superabsorbers and at least one coating layer with at least one biocide. In a preferred embodiment, the base polymer further comprises at least one coating layer with an additive, preferably a hardener (for closing-off). In another preferred embodiment at least one of these coating layers further comprises gelatin. In a more preferred embodiment of the invention all layers further comprise gelatin.

In another embodiment of the present invention the polymer composite material can withstand at least 12 months of outside exposure to sunlight and weather. That is independent on whether there is a coating layer present or not. By having such a minimum resistance the polymer compound is sure to fulfill the requirements of the intended use in agriculture as fumigation or mulch film or as reusable trays for seedling production (nursery trays), for instance.

In an aspect, the polymer composite material is not be biodegradable. In another aspect, the polymer composite material is not water soluble. In an aspect, the function of the polymer composite material is usable over a long period of time so that for example no weeds, pests or fungi can harm the plants as they grow in a field under the protection of the polymer composite biocide material. In an aspect, the articles of the intended use like films and trays can be useable over a wider period of time and do not degrade in one planting and harvesting season, for example. In an aspect, the mechanical stability of the films should be kept high because the film should preferably be retractable from the field and reusable.

It is within the scope of the inventive polymer composite material that additional pigments, additives and fillers can be used which are widely known to the skilled person.

Another subject of the present invention is a method for the production of a polymer composite material according to the present invention including the steps of mixing at least one base polymer compound and at least one biocide active ingredient so that the biocide active ingredient is incorporated in form of a molecular dispersion, forming the polymer composite material in the desired shape by molding and/or film formation via extrusion or blow molding.

There are four basic methods used for mixing plastics with the biocide active ingredients: dry mixer, batch mixer, continuous mixer, and screw extruder. The selection of the method determined by the condition of the material, the volume of end product required, and the sensitivity of the biocide active ingredients to shear stress and temperature of a polymer melt. The compounding process includes two stages: (1), mixing the materials and (2) forming the mixture into pellets, sheets, rods, or lumps for further processing by molding and/or film formation.

The present invention comprises therefore a polymer composite material, wherein the biocide active ingredient is incorporated in the polymer composite material in form of a molecular dispersion.

Alternatively, a polymer composite material according to the present invention can also be produced by a method for its production including the steps of mixing at least one coating compound and at least one biocide active ingredient so that the biocide active ingredient is incorporated in form of a molecular dispersion, coating the base polymer compound with the above mixture and curing the mixture to give a coating layer.

In an aspect, the present invention comprises therefore a polymer composite material, wherein the biocide active ingredient is incorporated into a coating layer.

The term "coating compound" refers to any possible compound or compounds that can be used to incorporate the at least one biocide active ingredient onto the base polymer. Particularly useful coating compounds according to the present invention are binders, such as superabsorbers and/or gelatin. In a preferred embodiment of the invention binders, preferably superabsorbers and gelatin and a hardener are used as coating compounds. In a further preferred embodiment the "coating compound" also comprises a carrier fluid.

The coating compounds can be applied to the workpiece made of the base polymer in a variety of ways. Coatings compounds can be sprayed over the part, or the part can be dipped into a tank of coating material. Other methods include showering parts with coatings or rolling parts between large barrels to spread on the coating.

Cascade casting or curtain casting advantageously allows the application of multiple layers, also of different thicknesses, onto the polymer composite material in a one work step.

The application of the coating layer is preferably carried out by curtain coating.

The method of curtain coating is well known in the field of photographic films and papers and can be advantageously applied to the coating of the present invention. Improved methods of curtain coating procedures that can be used to produce the polymer composite material of the present invention includes such procedures as they are described in EP 1 023 949 A1, EP 938 935 A2, U.S. Pat. No. 5,906,865, DE 195 00 402, and EP 275 015 B1, which are therefore incorporated by reference.

In the process of curtain coating, a base film or paper web is moved continuously by a transport device through a coating zone and is thereby coated with one or more layers either wholly or partially by the free-falling liquid curtain.

In the photographic industry, this process is used, for example, to apply photosensitive and non-photosensitive coatings. These coatings comprise mostly multiple layers formed from aqueous coating solutions which are coated as layer composites in the liquid state onto the base. The curtain in the curtain-coating process can be wider or narrower than the base. The base of the photographic application is mostly a synthetic film or a paper web. Coating speeds can vary in accordance with the base material and thickness and with the thickness of the liquid curtain and its viscosity, for example. In so called high coating speed applications the photographic coating solutions can be applied at a base speed from more than 250 meters per minute. The coated base then passes through a drying device in which the coating solution is dried. The dry film web is wound up. At this point, the edges of the web must be dry or else the individual layers of the roll will adhere.

With the advantageous possibility of producing the polymer composite material of the present invention by curtain coating the base polymer compound with at least one coating layer comprising at least one biocide, binder(s), carrier fluid and optionally additives, high production speed and low cost bulk production can be achieved.

In a preferred embodiment, curtain coating on a preferably Corona treated base polymer with a first coating comprising a binder, preferably a superabsorber and a carrier fluid and a second coating comprising at least one biocide and a carrier fluid is conducted. In a another preferred embodiment, the first coating with the binder further comprises gelatin and/or the second coating with the at least one biocide comprises gelatin. In an additional preferred embodiment, a hardener as an additive is added shortly before curtain coating to one of the coatings. A further preferred curtain coating method is conducted with a third coating comprising a hardener as an additive and a carrier fluid. In another preferred embodiment, the third coating comprises gelatin, carrier fluid and a hardener as an additive and the hardener is added to the gelatin and the carrier fluid shortly before the curtain coating. In another aspect, the disclosure provides for a curtain coating method conducted with a third coating comprising at least one biocide and optionally gelatin and a carrier fluid.

Preferably, any of the methods according to the present invention comprises the further step of coating both sides of the base polymer compound with a different mixture each comprising at least one biocide active ingredient. Like that, it is possible to incorporate different biocide active ingredients, one for instance for the disinfection of the soil or for the root protection of the plants and the other one as pesticide and/or fungicide directed to the surface of the agricultural field.

As already shortly mentioned above, a polymer composite material according to present invention or a product obtained by a method according to the present invention can be preferably used in agriculture and/or horticulture.

Especially the use as mulch film, fumigation film, or as propagation film is preferred.

Alternatively, a polymer composite material according to present invention or a product obtained by a method according to the present invention can be used as propagation pots, nursery trays, and/or harvest trays.

The invention also relates to mulch film, fumigation film, propagation film, propagation pots, nursery trays and/or harvest trays comprising a polymer composite material as discussed herein.

In another aspect, the disclosure provides for a polymer composite film for use in agricultural fumigation methods that has an improved barrier functionality, a good processability, and a long lifespan together with a reduced stiffness and a reduced tendency to roll up. In an aspect, the disclosure provides for a method for the production of such a polymer composite film. An example of a polymer composite film with barrier functionality may be found in U.S. patent application Ser. No. 12/175,276, filed Jul. 17, 2008, which is herein incorporated by reference in its entirety.

In an aspect, a polymer composite film with barrier functionality includes at least one base polymer compound and at least one barrier functional layer. In another aspect, the barrier functional layer includes at least one binder that is cross-linkable and after cross-linking capable of water absorbing and gel-forming. In yet another aspect, the binder is capable of absorbing at least about 15 or about 25 times its weight in an aqueous solution containing 0.9 weight percent sodium chloride. In another aspect, the binder is a superabsorbent polymer such as a polyacrylate.

Under the term barrier functional layer there are all polymer based coating layers understood which are capable of building a water barrier especially to the permeation of fumigation gases which are emitted by diffusion from fumigated soil. In another preferred embodiment of the invention the barrier functional layer comprises water and a superabsorbent polymer which is capable of a water take-up of at least least 100 weight % per gram polymer.

Fumigation is a method of pest control that fills an area with gaseous pesticides to suffocate or poison the pests within. It is utilized for control of pests in buildings, soil, grain, and produce, and is also used during processing of goods to be imported or exported to prevent transfer of exotic organisms. In an aspect, a rubber or polymer film is placed over an area to be treated. This aspect of the invention provides improved materials to do this. This concentrates the gases as well as keeps them from escaping and doing harm to people and wildlife in the neighbourhood.

Methyl bromide was among the most widely used fumigants until its production and use was restricted by the Montreal Protocol due to its role in ozone depletion. Other widely used fumigants include phosphine, 1,3-dichloropropene, chloropicrin, methyl isocyanate, methyl iodide, hydrogen cyanide, sulfuryl fluoride, hydrogen disulphide and formaldehyde.

Fumigation usually involves the following phases. First the area to be fumigated is usually covered to create a sealed environment; next the fumigant is released into the space to be fumigated; then, the space is held for a set period while the fumigant gas percolates through the space and acts on and kills any infestation in the area, next the space is ventilated so that the poisonous gases are allowed to escape from the space, and render it safe to enter. In an aspect, the above fumigation method can be used with any of the disclosed polymer composite materials described herein.

Advantageously, the polymer composite material with the barrier functional layer of the present invention is capable of securing the confinement of fumigation chemicals over a long period of time while still retaining good processability and a long life span. By employing a barrier functional layer comprising at least one binder that is cross-linkable and after cross-linking capable of water absorbing and gel-forming, the permeability of the fumigation chemicals is strongly reduced. The inventive combination with at least one binder that is cross-linkable and after cross-linking capable of water absorbing and gel-forming for the barrier layer facilities that water is absorbed during use but also prevents that the absorbed water is evaporated even in the harshest conditions. Apart from that, due to the barrier coating layer a much easier handling of the inventive film is achieved by reducing the stiffness and the tendency to roll up.

In an aspect, the barrier coating layer of the present invention is formulated from three components: binders, additives and a carrier fluid. In an aspect, the barrier coating layer should show the same resistance to outdoor exposure as the base polymer compound.

In another embodiment of the invention, the base polymer (preferably in the form of a film) is at least on one side Corona treated and comprises at least on one side at least one layer with a binder, preferably superabsorbers and more preferably polyacrylates. In an embodiment, the base polymer further comprises at least on one side at least one coating layer with an additive, preferably a hardener. In another embodiment at least one of these coating layers further comprises gelatin. In another embodiment of the invention all layers further comprise gelatin. In another embodiment of the invention, the base polymer further comprises at least one coating layer with at least one organic biocide.

The polymer composite material according to another embodiment of the present invention can be a multilayer coating structure and the barrier functional layer is incorporated into repeating coating layers. As an example, different binders can be incorporated in different layers or a layer can comprise different binders. An embodiment of the invention comprises a polymer composite material wherein the polymer composite material is of a multilayer coating structure and wherein the same or different barrier functional layers are incorporated into repeating coating layers.

By the incorporation of the barrier functional layer into repeating coating layers a control of the confinement rates maybe even better achievable. Apart from that, different barrier functional layers can be incorporated so that even scratches and superficial damages of the film do not impart the safe containment of the potentially hazardous chemicals.

In another preferred embodiment of the present invention an organic biocide is added to the barrier functional layer.

The coating layer can not only confine the fumigation chemicals and thus reduce the amount needed for effective treatment but it can also prevent the soil from being infested again. Accordingly, even less chemical is needed to achieve the desired effect.

In another embodiment of the present invention the polymer composite material can withstand at least 24 months of outside exposure to sunlight and weather. That is independent on whether there is a coating layer present or not. By having such a minimum resistance the polymer compound fulfils the requirements of the intended use in agriculture as fumigation or mulch film, for instance.

In another embodiment of the present invention the barrier functional layer is capable of absorbing water to comprise a water barrier of at least 0.4 mm thickness. Thus, a minimal confinement can be provided even over a long period of time and in hot weather conditions.

Another subject of the present invention is a method for the production of a polymer composite material according to the present invention including coating the base polymer compound with at least one barrier functional compound comprising a carrier fluid and a binder, preferably a superabsobent polymer, more preferably a polyacrylate polymer and curing the mixture to give a coating layer.

The "barrier functional compound" preferably further comprises gelatin. In a preferred embodiment of the invention, binders, preferably superabsorbers, more preferably polyacrylates, gelatin and as an additive a hardener are used as barrier functional compounds.

In an aspect, the method according to the present invention includes the further step of coating both sides of the base polymer compound with a different mixture each comprising at least one barrier functional layer. In an aspect, it is possible to incorporate different barrier functional layers, one for instance for the direct uptake of chemicals diffused from the soil and the other one as further confinement layer on the outer surface of the film.

In an aspect, a polymer composite material according to present invention or a product obtained by a method according to the present invention can be preferably used in agriculture as confinement film for fumigation methods.

In an aspect, the disclosure provides for a method of using a polymer composite material or composition disclosed herein to control, prevent, or inhibit the growth or infestation of weeds or vegetation. The disclosure also provides for a method of using a polymer composite film described herein to control, prevent, or inhibit weeds from piercing or puncturing a film covering, such as a polymer or plastic film.

The disclosure also provides for a method of using a polymer composite material or composition disclosed herein together with a biocide to control, prevent, or inhibit the growth or infestation of weeds or vegetation. Any biocide disclosed herein is capable of being used in the methods described herein, for example, halosulfuronmethyl or ethoxysulfuron. In a further aspect, a polymer composite film embedded with a biocide as described herein is more effective at controlling, preventing, or inhibiting the growth or infestation of vegetation or weeds, such as nutsedge, as compared to a conventional plastic mulch or a VIF ("virtually impenetrable film") plus an herbicide. Without being limited, Cadillac Virtually Impenetrable Film is a type of VIF.

In an aspect, a polymer composite material described herein does not include a biocide or herbicide. In another aspect, the polymer composite material is substantially free of biocide or herbicide. In yet another aspect, the disclosure further provides for a polymer composite material with a composition of less than 0.001%, 0.01%, 0.1%, 0.1%, 0.5% 1.0%, 2.0%, 5%, 10%, or 20% by weight of a herbicide or biocide.

A polymer composite film described herein without an herbicide or biocide can be used in any of the methods described herein. For example, the use of a polymer composite material described herein without a biocide can be used in methods of controlling, preventing, or inhibiting the growth or infestation of weeds, such as nutsedge. In yet another aspect, the use of a polymer composite film described herein without the incorporation of an herbicide is more effective at controlling, preventing, or inhibiting the growth or infestation of weeds, such as nutsedge, as compared to a conventional plastic mulch or a VIF without a herbicide. As set forth in FIG. 1, for example, a polymer composite material described herein without an herbicide ("Film A Blank") is more effective at controlling, preventing, or inhibiting the growth of weeds, such as nutsedge, than a VIF. As described in FIG. 1, fewer nutsedge weeds penetrate or pierce the plastic covering when a polymer composite film described herein without an herbicide is used as compared to a VIF. In another aspect, the polymer composite material described herein reduces the number of weeds that penetrate, pierce, or disrupt the plastic by about 5%, 10%, 20%, 30%, 40%, 50%, 60%, 70%, 80%, 90% o, 95% or more as compared to a conventional plastic covering material or VIF.

A biocide can be applied directly to soil, a crop, a weed, fruit, vegetable, vegetation, or combinations thereof before or after application of a polymer composite film as described herein. In an aspect, a fumigant is applied to soil, a crop, a weed, or vegetation before or after application of a polymer composite film as described herein. In yet another aspect, the biocide is released over a period of about 1, 2, 5, 10, 20, 30, 50, 100, or 200 days from a polymer composite material.

In a further aspect, a polymer composite material as described herein is more effective at controlling, preventing, or inhibiting the growth or infestation of vegetation or weeds, such as nutsedge, as compared to a conventional plastic mulch or a VIF after about 1, 5, 10, 15, 20, 25, 20, 35, 40, 50, 60, 75, or 100 days of polymer composite material application. In an aspect, the control or inhibition of nutsedge growth using the method of the present invention is more effective than in a similar method using a conventional plastic mulch film or VIF applied over an equal area of soil to which halosulfuronmethyl and/or ethoxysulfuron has been spray applied in the same amount as that present in the polymer composite material. In another aspect, the polymer composite material described herein reduces the growth of weeds by about 10%, 20%, 30%, 40%, 50%, 60%, 70%, 80%, 90% or more as compared to a conventional plastic covering material or VIF.

The disclosure also provides for a method of using a polymer composite material or composition disclosed herein to control, prevent, or inhibit the growth of a weed that is destructive to a plastic or polymer film. In another aspect, the weed is nutsedge. Nutsedges are very aggressive and persistent weeds that commonly infest lawns, vegetable and flower gardens, and home landscapes. Many nutsedges are perennials whose leaves die back in the fall when temperatures decrease. Tubers (often called "nutlets") and rhizomes (underground stems) survive in the soil and sprout the following spring. The tubers and rhizomes can grow eight to 14 inches below the soil surface. Nutsedges thrive in almost any kind of soil. While they prefer moist soil, established nutsedge plants will thrive even in dry soil. Nutsedges may spread by small tubers, by creeping rhizomes or by seed. New tubers begin forming four to six weeks after a new shoot emerges. Individual nutsedge plants may eventually form patches 10 feet or more in diameter.

Purple nutsedge (*Cyperus rotundus*) and yellow nutsedge (*Cyperus esculentus*) are common nutsedges. Yellow nutsedge is more widespread than purple nutsedge due to its greater cold tolerance. However, where purple nutsedge is adapted, it can be even more vigorous than yellow nutsedge. The two species often grow together. They can be very difficult to eradicate and their control is often a long process.

In an aspect, a method is provided of inhibiting the growth of nutsedge in an area of soil, including applying a mulch film, fumigation film, and/or propagation film to an area of soil, wherein the film includes a polymer composite material including at least one base polymer compound with at least one coating layer.

The coating layers can be any of those disclosed above, and can include gelatin, at least one binder, at least one additive, and/or at least one carrier fluid. These components may be present in one or more different coating layers, alone or in various combinations with each other. In certain embodiments, at least one coating layer contains at least one biocide active ingredient including an organic biocide that can be emitted from the polymer composite material by diffusion and/or osmosis. Halosulfuronmethyl and/or ethoxysulfuron are particularly effective for inhibiting the growth of nutsedge in the method of the present invention, and can be present individually or in combination in the same or different coating layers of the polymer composite material.

In an aspect, the disclosure provides for a method of increasing crop safety or protecting crops by using a polymer composite material disclosed herein. The disclosure also provides for a method of protecting crops from a weed or other infestation by using a polymer composite material disclosed herein. In another aspect, the disclosure provides for a method of protecting crops from insect infestation, such as nematode infestation, by using a polymer composite material described herein.

In another aspect, the disclosure provides for a method of increasing crop safety or protecting crops by using a polymer composite material disclosed herein. In an aspect, the crop safety is increased relative to a conventional plastic mulch film or VIF. The disclosure also provides for a method of improving crop safety by using a polymer composite material as described herein relative to a conventional plastic mulch film or VIF applied over an equal area to which the same biocide active ingredient has been spray applied pre-emergence in the same amount as in the polymer composite material.

The disclosure also provides for a method of increasing crop yield by using a polymer composite material disclosed herein. In an aspect, the disclosure provides for a method of increasing the yield of fruits and vegetables by using a polymer composite material as described herein. Without being limited, examples of fruits or vegetables suitable for use with the methods disclosed herein include tomato, bell pepper, eggplant, zucchini, watermelon, cantaloupe, collards, or strawberries. In yet another aspect, the yield of a crop can be improved by protecting a crop from a weed by using a polymer composite material disclosed herein. As an example, the safety and yield of a crop can be improved by protecting a crop from weeds that destroy plastic film or plastic mulch.

In another aspect, the disclosure provides for a method of increasing crop safety, increasing crop yield, or protecting crops by applying a plastic film, mulch film, fumigation film, propagation film, or polymer composite film, wherein the film includes a polymer composite material comprising at least one base polymer compound, at least one biocide active ingredient, and at least one coating layer.

The coating layers may be any of those disclosed above, and may include gelatin, at least one binder, at least one additive, and/or at least one carrier fluid. These components can be present in one or more different coating layers, alone or in various combinations with each other. In certain embodiments, at least one coating layer contains at least one biocide active ingredient comprising an organic biocide that can be emitted from the polymer composite material by diffusion and/or osmosis. Halosulfuronmethyl and/or ethoxysulfuron are particularly effective, and may be present individually or in combination in the same or different coating layers of the polymer composite material. In another aspect, the biocide is applied to a crop or soil surface prior to the application of a plastic film.

It has been observed in the method of the present invention, where biocide active ingredients are present in the film and not applied directly to plants or soil, that increased crop safety is more effective than in a similar method using a conventional plastic mulch film applied over an equal area of soil to which the same biocide active ingredient has been spray applied, pre-emergence, in the same amount as that present in the polymer composite material of the film.

Without being limited, increased crop safety can be demonstrated in a number of ways; for example, reduced injury due to over-exposure to biocide active ingredient as described above, production of healthier plants, and increased yield.

In an aspect, the disclosure provides for a method of reducing or limiting fumigant dosage in crop protection or weed control by applying a polymer composite film as described herein to soil, vegetation, or a crop. In another aspect, the polymer composite film includes at least one base polymer compound and at least one barrier functional layer. In another aspect, the barrier functional layer includes at least one binder that is cross-linkable and after cross-linking capable of water absorbing and gel-forming. In yet another aspect, the binder is capable of absorbing at least about 15 or about 25 times its weight in an aqueous solution containing 0.9 weight percent sodium chloride.

In an aspect, the disclosure provides for a method of reducing or eliminating fumigant dosage in crop protection or weed control by applying a polymer composite material as described herein to soil, a weed, a crop, or vegetation. In another aspect, the polymer composite material includes a base polymer compound coated with
  (1) a first barrier layer;
  (2) a second layer;
  (3) a third protective layer; and
wherein the application of the polymer composite material reduces the amount of fumigant dosage necessary to control weed growth.

In an aspect, a biocide is present in the polymer composite material. In another aspect, the biocide is present in one or more of coating layers one, two, or three. In another aspect, the biocide includes halosulfuronmethyl, ethoxysulfuron, or combinations thereof and the weed to be controlled is nutsedge.

The disclosure also provides for a method of reducing the fumigant dose needed to protect a crop or control the growth of a weed by about 10% or more, about 20% or more, about 30% or more, about 40% or more, about 50% or more, about 60% or more, about 70% or more, about 80% or more, or about 90% or more. Also envisioned is a method of eliminating the use of a fumigant or where the use of a fumigant is substantially reduced. In another aspect, the fumigant dose is reduced relative to a VIF with or without an herbicide.

Without being limited, as an example, the disclosure also provides for a polymer composite material including a base material and a coating based on the following.

In an aspect, the disclosure provides for a polymer composite material comprising, consisting of, or consisting essentially of a base polymer coated with:
  (1) a first barrier layer;
  (2) a second layer; and
  (3) a third protective layer.

In another aspect, the disclosure provides for a polymer composite material comprising, consisting of, or consisting essentially of a base polymer coated with:
  (1) a first barrier layer including a superabsorber;
  (2) a second layer including a binder and optionally a biocide; and
  (3) a third protective layer including a binder and a hardener.

In another aspect, the disclosure provides for a polymer composite material comprising, consisting of, or consisting essentially of a base polymer coated with:
(1) a first layer including a binder, superabsorber, or combinations thereof;
(2) a second layer including a water soluble chemical and/or physical cross-linkable adhesive polymers and optionally a biocide; and
(3) a third layer including a water soluble chemical and/or physical cross-linkable adhesive polymers protective layer.

In another aspect, the disclosure provides for a polymer composite material comprising, consisting of, or consisting essentially of a base polymer coated with:
(1) a first layer including a binder, such as a polyacrylate or a cross linked sodium polyacrylate;
(2) a second layer including gelatin and optionally a biocide; and
(3) a third layer including gelatin, a hardener, and/or a carrier fluid.

In another aspect, the disclosure provides for a polymer composite material comprising, consisting of, or consisting essentially of a base polymer coated with:
(1) a first layer including a binder, such as a polyacrylate or a cross linked sodium polyacrylate;
(2) a second layer including a binder, such as a polyacrylate or a cross linked sodium polyacrylate;
(3) a third layer including gelatin and optionally a biocide; and
(4) a fourth layer including gelatin, a hardener, and/or a carrier fluid.

In an aspect, the above polymer composite material with three or four layers can be used in any of the methods described herein.

Any of the disclosed binders, biocides, carrier fluids, or other components may be used in the aforementioned coating layers. In an aspect, any of the disclosed base polymers may be coated with the aforementioned coating layers. In another aspect, the first layer or barrier layer can include any of the disclosed binders, superabsorber compounds, or water absorbent cross-linkable polymers. The disclosure also provides that any binder, gel-forming compound, or water absorbing cross-linkable coating binder as disclosed herein may be used in the second layer. In another aspect, any biocide or herbicide disclosed herein can be used in the second layer. In yet another aspect, the protective layer, for example, the third layer in a three-layer coating, can include any of the disclosed binders, superabsorber compounds, or water absorbent cross-linkable polymers, together with a carrier or hardener.

The disclosure also provides for a polymer composite material comprising, consisting of, or consisting essentially of a base polymer coated with one, two, three, four, five, six, seven, eight, nine, ten, fifteen, or twenty or more coating layers as described herein. In an aspect, a biocide can be present in any of the coating layer(s). In yet another aspect, the outermost coating layer is a protective layer including, for example, a binder, a hardener, or combinations thereof. The disclosure also provides for the presence of a biocide or herbicide in the second outermost layer. In another aspect, a biocide or herbicide is not present in any of the coating layers. In an aspect, the coating layers are stacked on top of one another with the first layer being coated on the base polymer and the final coating the outermost coating.

In an aspect, at least one biocide is present in the first coating layer, the second coating layer, the third coating, the fourth coating layer, the fifth coating layer, the six coating, the seventh coating layer, the eighth coating layer, the ninth coating, the tenth, fifteenth coating layer, and/or the twentieth coating layer. In another aspect, one, two, or three or more biocide compounds can be present in any of the above layers. In an aspect, the biocide can be released by a controlled release, time released, prolonged release, delayed release, rapid release mechanism, or combinations thereof.

The disclosure also provides for a polymer composite material as described herein containing a biocide or herbicide, such that the biocide or herbicide is present in the polymer composite material or released from the polymer composite material in an amount equivalent to from about 20-40, 25-45, 10-50, 20 to 100, 50 to 200, 100-300, or 20 to 500 grams/hectare. In another aspect, the disclosure provides for a polymer composite material as described herein containing a biocide or herbicide, such that the biocide or herbicide is present in the polymer composite material in an amount equivalent to from about 0.001-0.01, 0.01-0.05, 0.05-0.10, 0.10-0.50, 0.50-1.0, 1.0-10, 10-100 or more ounces/acre. In yet another aspect, the biocide or herbicide is present in a concentration of about 0.45-0.55, 4-0.6, 0.3-0.8, 0.4-0.6, 01-1.0, 0.2-1.0, 0.5-2.0, or more oz ai/ac. In another aspect, the biocide or herbicide is present in a concentration of about 0.563 oz ai/ac.

In another aspect, any of the polymer composite material comprising, consisting of, or consisting essentially of a base polymer coated with one, two, three, four, five, six, seven, eight, nine, ten, fifteen, or twenty layers can be used with any of the methods set forth herein.

EXAMPLES

Example 1

Manufacturing of Propagation Films

Propagation films by coating a polyethylene film with following additional layers was manufactured by using a curtain casting machine:

Film 1:
Base: Corona treated 100 μm thick Low-density polyethylene (LDPE) polyethylene film
First layer: 9.36 g/m$^2$ superabsorber S1 (flexible absorbent binder composed of: 20-40% by weight Sodium Polyacrylate (CAS-No.: 9003-04-7), 2-5% by weight polyethylene glycol (CAS-No.: 25322-68-3), water (CAS-No.: 7732-18-5) dissolved in 53.40 g water
Second layer: 9.36 g/m$^2$ superabsorber S1 dissolved in 53.40 g water
Third layer: 9.36 g/m$^2$ superabsorber S1 dissolved in 53.40 g water
Fourth layer: 9.36 g/m$^2$ superabsorber S1 dissolved in 53.40 g water Film 2:
Base: Corona treated 100 μm thick Low-density polyethylene (LDPE) polyethylene film
First layer: 9.36 g/m$^2$ superabsorber S1 and 3.12 g/m$^2$ gelatin dissolved in 53.40 g water
Second layer: 9.36 g/m$^2$ superabsorber S1 and 3.12 g/m$^2$ gelatin dissolved in 53.40 g water
Third layer: 9.36 g/m$^2$ superabsorber S1 and 3.12 g/m$^2$ gelatin dissolved in 53.40 g water
Fourth layer: 9.36 g/m$^2$ superabsorber S1 and 3.12 g/m$^2$ gelatin dissolved in 53.40 g water
Fifth layer: 2.34 g/m$^2$ gelatin dissolved in 27.53 g water
Sixth layer: 1.20 g/m$^2$ gelatin 1.33 g/m² hardener H1 (formaldehyde, concentration: 10% in water; coating amount 0.086 g hardener H1 per g gelatin). Gelatin and hardener are premixed shortly before curtain coating with 28.20 g water Film 3:

Base: Corona treated 100 μm thick Low-density polyethylene (LDPE) polyethylene film First layer: 9.36 g/m² superabsorber S1 and 3.12 g/m² gelatin dissolved in 26.70 g water Second layer: 9.36 g/m² superabsorber S1 and 3.12 g/m² gelatin dissolved in 26.70 g water Third layer: 9.36 g/m² superabsorber S1 and 3.12 g/m² gelatin dissolved in 26.70 g water Fourth layer: 9.36 g/m² superabsorber S1 and 3.12 g/m² gelatin dissolved in 26.70 g water Fifth layer: 2.34 g/m² gelatin dissolved in 27.53 g water Sixth layer: 1.2 g/m² gelatin, 1.33 g/m² hardener H1 premixed shortly before curtain coating with 28.20 g water.

After coating, the films were dried.

Example 2

Mechanic Stability of the Films

Then, the films prepared according to example 1 were soaked for 10 minutes in distilled water. Subsequently, excessive water was drained and the mechanic stability was tested by washing-up the soaked layers with flowing warm water. Whereas the superabsorber S1 layers dissolve from the polyethylene layer in film 1, the additional layers in films 2 and 3 do not dissolve from the polyethylene layer.

Example 3

Manufacturing of Fumigation Films with Biocides

According to similar methods as described in example 1, following six fumigation films were manufactured with the following final coating thickness after drying Base: Corona treated 100 μm thick high-density polyethylene (HDPE) film First layer: 6 μm superabsorber binder
Second layer: 6 μm superabsorber binder
Third layer: 6 μm superabsorber binder
Fourth layer: 6 μm superabsorber binder
Fifth layer: 3 μm gelatin with herbicide
Sixth layer: 3 μm gelatin hardened Following different herbicides were introduced in the fifth layer: placebo (film 1), aclonifen (150 mg/m²; film 2), ethoxysulfuron (6 mg/m²; film 3), isoxaflutole (10 mg/m2; film 4), benfuresate (150 mg/m²; film 5), glyphosate (200 mg/m², film 6), Halosulfuronmethyl (5 mg/m², film 7).

Example 4

Manufacturing of Fumigation Films with Biocides

Low density polyethylene were dry blended with 7 percent by weight of a commercial stabilizer LDPE masterbatch with Titanium dioxide pigments and HALS UV stabilizer, e.g. PLASTWITTE PE 7344 from Cabot Deutschland and the specified amount of, the selected herbicide, extruded and chopped to form molding pellets. The molding pellets were placed in a standard blow molding apparatus and the thermoplastic composition was blown into a film in accordance with conventional procedures at temperatures between 160 and 240° C. depending on the decomposition and/or boiling temperature of the selected herbicide. Sample sections of the various films of uniform surface area and uniform 100 μm thickness were used for all tests.

Films without herbicide (film 8), and with Ethoxysulfuron (6 mg/m²; film 9) and benfuresate (150 mg/m²; film 10) were blow molded from the above mixtures and tested.

Table 1 indicates the physicals properties of the films according to example 8, 9 and 10.

TABLE 1

| Properties | ASTM Method | Units (SI) | Typical Value |
|---|---|---|---|
| Resin Properties Example 8/9/10 | | | |
| Melt Index | D 1238 | g/10 min. | 1.8/1.8/1.8 |
| Density | D 1505 | g/cm³ | 0.923/0.922/0.922 |
| Melting Point | — | ° C. | 110/110/110 |
| Film Properties Example 8/9/10 | | | |
| Tensile Strength @ Break | | | |
| MD | D 882 | % | 4000/4010/4001 |
| TD | D 882 | % | 3400/3402/3398 |
| Elongation @ Break | | | |
| MD | D 882 | % | 300/298/301 |
| TD | D 882 | % | 500/500/500 |
| 1% Secant Modulus | | | |
| MD | D 882 | % | 26000/26100/26002 |
| TD | D 882 | % | 30000/30000/30000 |
| Dart Drop Impact Strength | D 1709 | g | 90/89/91 |
| Elmendorf Tear Strength | | | |
| MD | D 1922 | g | 360/360/359 |
| TD | D 1922 | g | 200/201/200 |

Example 5

Improvement of Weed Control

Soil filled trays with a range of weeds including the key problem weeds of CYPES (Yellow Nut Sedge, *Cyperus esculentus*), and CONAR (Field Bindweed, *Convolvulus arvensis*) were used for a glass house trial with the plastic fumigation films (comprising biocides) manufactured according to example 4.

Soil was filled in to plastic trays until they were approximately ¾ full and then the soil lightly compressed. Even amounts of CYPES and CONAR weed seeds were then sown out on several sets of these trays and then the seeds covered with soil until the trays were completely full. These filled trays were then covered with the different plastic fumigation films and as a control an untreated placebo plastic film. Light weights were placed on the plastic film to ensure that the film was not pushed up or away via weed growth.

The filled and covered trays were placed in a glasshouse with a 12 hour day and 12 hour night regime. Day temperatures were 24. degree. C. and a relative humidity of 60% and night temperatures were 16. degree. C. also with 60% relative humidity. The light intensity is up to 60,000 Lux. The plants were irrigated via flood irrigation (water from below) daily so that good growth of the plants could be assured. Plant growth was monitored via 2 reps of each weed species that were not covered with plastic film.

After 4 weeks the weights and the plastic films were removed and a visual assessment of the weed control was conducted. The trays covered with treated plastic film were compared to the trays covered with untreated plastic film. A mean of the two reps per treatment was made and is shown below in table 2. Values given are in percent 0=No efficacy; 100=Complete Kill.

TABLE 2

| Plastic Sheet | Biocide Concentration kg ai/ha | Percent CYPES | Efficacy CONAR |
|---|---|---|---|
| Placebo Film (film 1) | | 0 | 0 |
| Aclonifen Folie (film 2) | 1.500 | 30 | 37.5 |
| Ethoxysulfuron (film 3) | 0.060 | 96 | 97 |
| Isoxaflutole (film 4) | 0.100 | 55 | 95.5 |
| Benfuresate (film 5) | 1.500 | 98 | 97.5 |
| Glyphosate (film 6) | 2.000 | 42.5 | 67.5 |
| Halosulfuronmethyl (film 7) | 0.053 | 96 | 65.0 |
| Placebo film (film 8) | | 0 | 0 |
| Ethoxysulfuron (film 9) | 0.060 | 89 | 90 |
| Benfuresate (film 10) | 1.500 | 91 | 92 |

All films comprising biocides showed medium to strong inhibition for both weeds over a period of at least 4 weeks.

Example 6

Weed Control without an Herbicide

The use of a polymer composite material according to the invention, Film A, with or without incorporation of an herbicide is evaluated verses conventional plastic mulch, VIF, or "virtually impenetrable film." The results of this analysis are set forth in FIG. 1. Film A contains a base polymer compound coated with:

(1) a first layer including cross linked sodium polyacrylate;

(2) a second layer including gelatin; and (3) a third layer including gelatin and a hardener.

As set forth in FIG. 1, "Film A HSM" contains Halosulfuronmethyl in the second layer; "Film A Blank" is Film A without a biocide; "Sandea" is a herbicide Halosulfuron (Sandea); "VIF" is "virtually impenetrable film," and "MeBR" is methyl bromide. Additionally, as set forth in FIG. 1, InLine® is a fungicide and nematicide (Dow Agrosciences).

Film A Blank is more effective at controlling the spread of nutsedge (*Cyperus* Supp.) as compared to the VIF without a herbicide. As described in FIG. 1, the first data column, "plant hole," represents the number of nutsedge creating a hole in the film, the middle data column, "through film," represents the number of nutsedge penetrating the film, and the final column, "total," represents the total number of nutsedge either creating a hole in the film ("plant hole") or the number of nutsedge penetrating the film ("through film").

Example 7

Weed Control and Reduction of Fumigation Dose

Figure 2:
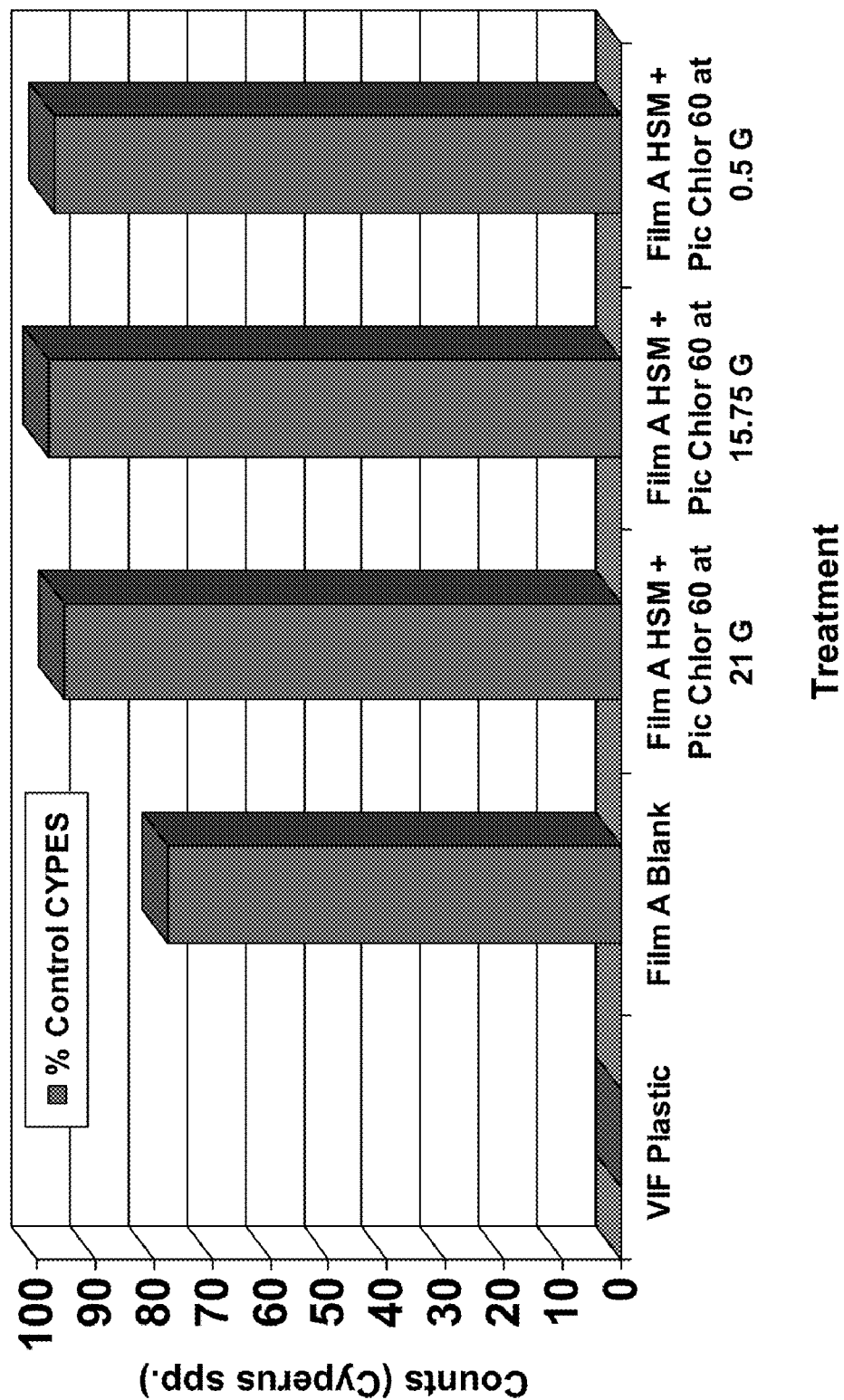
FIG. 2 provides an analysis of weed control of a polymer composite material according to the disclosure together with varying amounts of a fumigant.
Figure 3:
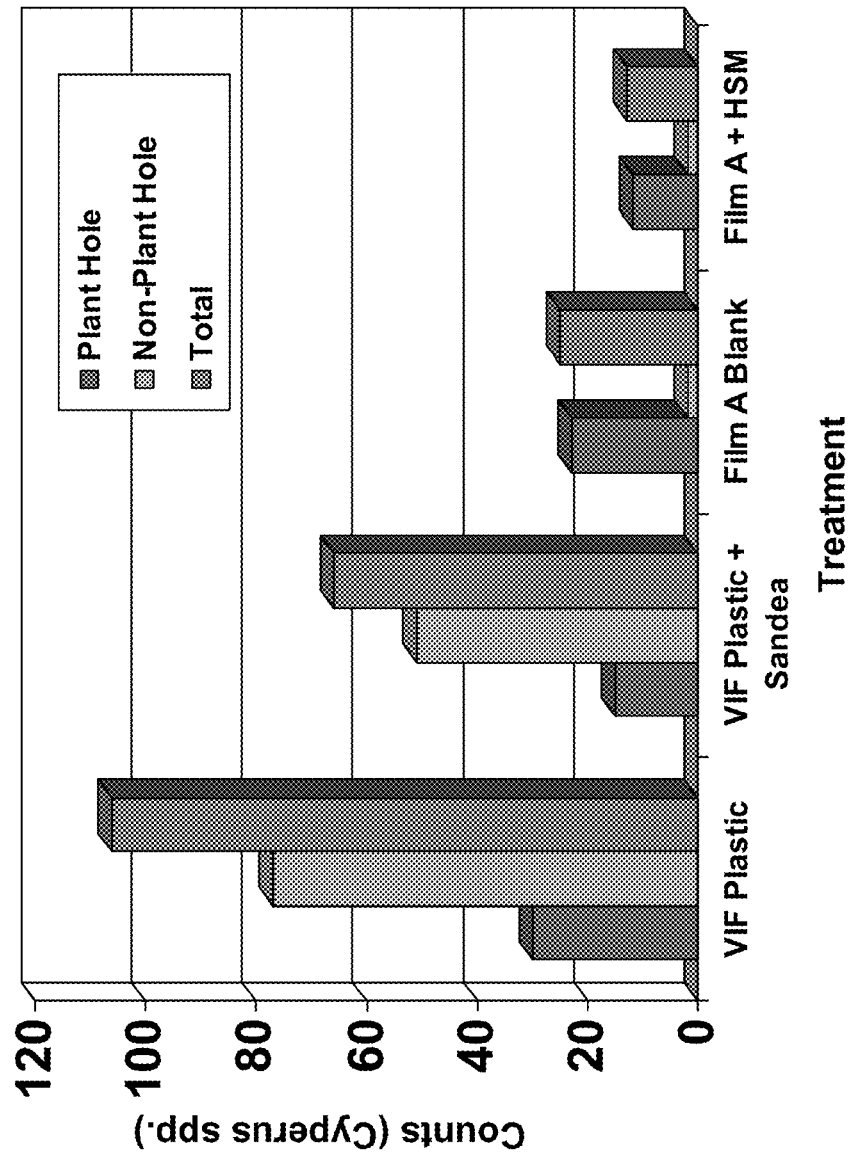
FIG. 3 provides an analysis of weed control of a polymer composite material according to the disclosure with or without incorporation of herbicide verses conventional plastic mulch or VIF.

The use of Film A without an herbicide ("Film A Blank") with halosulfuronmethyl and various concentrations of fumigant (0.5 g, 15.75 g, and 21 g of Pic Chlor 60) is evaluated verses conventional plastic mulch, VIF, in FIG. 2. Film A Blank and Film A-HSM with 0.5 g, 15.75 g, and 21 g of Pic Chlor 60 is more effective at controlling the spread of the nutsedge (Cyperus Supp.) than VIF.

Example 8

Weed Control using Polymer Composite Material with Halosulfuron-methyl, Ethoxysulfuron herbicide, or Halosulfuron (Sandea)

The influence of Film A with Halosulfuron-methyl on yellow nutsedge is evaluated in Table 3. As set forth in Table 3, Film A equipped with Halosulfuron ("Film A-HSM") provides better control of yellow nutsedge than a similar treatment containing a VIF mulch plus the same dose of Halosulfuron-methyl sprayed to the bed surface before Film A plastic installation.

TABLE 3

| | % Infested Bed Tops | | | |
|---|---|---|---|---|
| Treatments | 1st rating | 2nd rating | 3rd rating | 4th rating |
| 1 Film A-HSM | 4.75 | 1.25 | 0.75 | 0.75 |
| 2 VIF*** + Sandea (Profine 75) | 17.5 | 70.30 | 35.00 | 42.50 |

***Plant Blockade VIF used in comparison to Film A.

The ability of Film A-HSM or Film A-Ethoxy (Film A with ethoxysulfuron) to control yellow nutsedge as compared to a VIF mulch plus the same dose of halosulfuronmethyl or ethoxysulfuron is evaluated in Table 4. Film A-HSM also exhibits improved control of yellow nutsedge compared to VIF Mulch plus a Halosulfuron (Sandea) with a bed top spray application (Table 3). As described in Tables 4 and 5, "UTC" corresponds to an "untreated control."

TABLE 4

| Treatment (oz ai/ac) | Biocide Concentration (oz ai/ac) | Control* of Yellow Nutsedge (63 Days after Application or DAA) |
|---|---|---|
| 1 Placebo Film (UTC) | | 0.3 |
| 2 UTC-No Film | | 91.0 |
| 3 Film A-Ethoxy | 0.215 | 0.0 |
| 4 Film A-Ethoxy | 0.429 | 0.5 |
| 5 Film A-Ethoxy | 0.644 | 0.3 |
| 6 Film A-Ethoxy | 0.859 | 0.5 |
| 7 VIF** Mulch + Ethoxy | Spray-0.644 | 2.8 |
| 8 VIF Mulch + HSM | Spray-0.563 | 4.3 |
| 9 Film A-HSM | | 0.0 |

*Ratings based on average numbers per plot of Cyperus esculentus (Yellow Nutsedge) counted above the plastic at 63 days after application.
**Cadillac VIF Film 1.25 ml thickness.

Example 9

Crop Safety

The crop safety profile of Film A equipped with either halosulfuron (Film A-HSM) or ethoxysulfuron (Film A-Ethoxy) is evaluated on a variety of fruits and vegetables, including tomato, bell pepper, eggplant, watermelon, cantaloupe, and collards. The results of this analysis are set forth in Tables 5 and 6. VIF was used as the control.

TABLE 5

| Treatment (oz ai/ac) | Percent Injury* | | |
|---|---|---|---|
| | Tomato (25 DAA) | Bell Pepper (40 DAA) | Eggplant (40 DAA) |
| 1 Placebo Film (UTC) | 0.0 | 0.0 | 0.0 |
| 2 UTC-No Film | 0.0 | 0.0 | 0.0 |
| 3 Film A-Ethoxy (0.215) | 5.3 | 15.0 | 0.0 |
| 4 Film A-Ethoxy (0.429) | 5.0 | 20.0 | 0.0 |
| 5 Film A-Ethoxy (0.644) | 8.3 | 20.0 | 11.7 |
| 6 Film A-Ethoxy (0.859) | 3.3 | 41.7 | 15.0 |
| 7 VIF Mulch + Ethoxy Spray (0.644) | 12.0 | 46.7 | 28.3 |
| 8 VIF Mulch + HSM Spray (0.563) | 9.7 | 26.7 | 15.0 |
| 9 Film A-HSM | 2.0 | 16.7 | 8.7 |

*On the days indicated, a percent injury of 0 is representative of "no effect"; a percent injury of 100 is representative of a "complete kill

TABLE 6

| Treatment (oz ai/ac) | Percent Injury* | | |
|---|---|---|---|
| | Watermelon (40 DAA) | Cantaloupe (40 DAA) | Collards (40 DAA) |
| 1 Placebo Film (UTC) | 0.0 | 0.0 | 0.0 |
| 2 UTC-No Film | 0.0 | 0.0 | 0.0 |
| 3 Film A-Ethoxy (0.215) | 10.0 | 8.3 | 10.7 |
| 4 Film A-Ethoxy (0.429) | 13.3 | 34.0 | 19.0 |
| 5 Film A-Ethoxy (0.644) | 30.0 | 63.3 | 33.3 |
| 6 Film A-Ethoxy (0.859) | 31.7 | 76.7 | 38.3 |
| 7 VIF Mulch + Ethoxy Spray (0.644) | 41.7 | 86.7 | 50.0 |
| 8 VIF Mulch + HSM Spay (0.563) | 6.7 | 5.0 | 83.3 |
| 9 Film A-HSM | 1.7 | 0.0 | 68.3 |

*On the days indicated, a percent injury of 0 is representative of "no effect"; a percent injury of 100 is representative of a "complete kill"

What is claimed is:

1. A method of protecting a crop from weed infestation comprising:
   applying a polymer composite material to soil, a weed, or combinations thereof, wherein said polymer composite material comprises a base polymer compound coated with
   (1) a first barrier layer comprising a polyacrylate;
   (2) a second layer comprising gelatin and a halosulfuronmethyl biocide; and
   (3) a third protective layer comprising gelatin and a formaldehyde hardener.

2. The method of claim 1, wherein the weed is nutsedge.

3. The method of claim 1, wherein the halosulfuronmethyl biocide is released in an amount to provide a concentration of 20 to 500 grams/hectare.

4. The method of claim 1, wherein said second layer further comprises an ethoxysulfuron biocide.

5. The method of claim 1, wherein crop safety is increased relative to a conventional plastic mulch film or virtually impenetrable film (VIF) with a biocide.

6. The method of claim 5, wherein the increased crop safety is more effective as compared to a conventional plastic mulch film or VIF applied over an equal area to which the same biocide active ingredient has been spray applied pre-emergence in the same amount as that present in the polymer composite material.

7. The method of claim 1, wherein crop yield is increased.

8. The method of claim 1, wherein the base polymer compound is a polyethylene.

9. The method of claim 8, wherein the base polymer compound has a thickness of 10 to 250 μm.

10. A method of reducing the growth of a weed, comprising: applying a polymer composite material comprising a base polymer compound and a halosulfuronmethyl biocide active ingredient to soil, or a weed,
    wherein the base polymer compound has one or more coating layers; and
    wherein said one or more coating layers comprises a polyacrylate, gelatin, and a formaldehyde hardener.

11. The method of claim 10, wherein said polymer composite material further comprises ethoxysulfuron.

12. The method of claim 10, wherein the base polymer compound is a polyethylene.

13. The method of claim 12, wherein the base polymer compound has a thickness of 10 to 250 μm.

14. The method of claim 10, wherein the halosulfuronmethyl biocide is released in an amount to provide a concentration of 20 to 500 grams/hectare.

* * * * *